US006599867B2

(12) United States Patent
Hammond et al.

(10) Patent No.: US 6,599,867 B2
(45) Date of Patent: Jul. 29, 2003

(54) OVERBASED DETERGENT ADDITIVES

(75) Inventors: Steve Hammond, Cheshire (GB); Mark A. Price, Oxfordshire (GB); Philip Skinner, Oxfordshire (GB)

(73) Assignee: Infineum International Ltd. (GB)

( * ) Notice: Subject to any disclaimer, the term of this patent is extended or adjusted under 35 U.S.C. 154(b) by 0 days.

(21) Appl. No.: 10/061,624

(22) Filed: Jan. 31, 2002

(65) Prior Publication Data

US 2002/0183212 A1 Dec. 5, 2002

(30) Foreign Application Priority Data

Feb. 16, 2001 (EP) .............................. 01301407

(51) Int. Cl.$^7$ ........................................ C10M 159/20
(52) U.S. Cl. ....................................... 508/460
(58) Field of Search ........................................ 508/460

(56) References Cited

U.S. PATENT DOCUMENTS

| | | | | |
|---|---|---|---|---|
| 4,824,585 A | | 4/1989 | Marotel et al. ............... 252/39 |
| 5,458,790 A | * | 10/1995 | Cane et al. .................. 508/460 |
| 6,103,672 A | * | 8/2000 | Dunn et al. .................. 508/185 |
| 6,153,565 A | * | 11/2000 | Skinner et al. ............. 508/391 |
| 6,348,438 B1 | * | 2/2002 | Le Coent et al. ........... 508/332 |
| 6,417,148 B1 | * | 7/2002 | Skinner et al. ............. 510/184 |
| 6,429,178 B1 | * | 8/2002 | Skinner et al. ............. 510/184 |

FOREIGN PATENT DOCUMENTS

| | | | |
|---|---|---|---|
| EP | 0 267 658 A2 | 5/1988 | ........... C07C/51/41 |
| EP | 0 657 523 A2 | 6/1995 | ........ C10M/159/22 |
| WO | WO97/46643 | 12/1997 | ........ C10M/159/20 |
| WO | WO97/46644 | 12/1997 | ........ C10M/159/20 |
| WO | WO97/46645 | 12/1997 | ........ C10M/159/22 |
| WO | WO97/46646 | 12/1997 | ........ C10M/159/22 |

* cited by examiner

Primary Examiner—Jacqueline V. Howard

(57) ABSTRACT

Overbased detergent additives for lubricating oils comprise an organic substantially aromatic carboxylate, such as an alkylsalicylate, as a surfactant and have a TBN of 200 or greater, an active ingredient content of 70 mass % or greater, a kinematic viscosity at 100° C. of less than 1000 $mm^2s^{-1}$ and a basicity index (BI) of less than 13.

14 Claims, No Drawings

OVERBASED DETERGENT ADDITIVES

The present invention relates to overbased alkaline earth metal detergent lubricant additives.

The use of alkaline earth metal salts of organic carboxylic acids as detergent additives for lubricating oil compositions (or lubricants) is known in the art. When applied in lubricating oil compositions, they ensure that the inside of engine cylinders remains clean and that the deposition of carbonaceous products on pistons and in piston grooves is counteracted, so that piston ring sticking is prevented. They are also known in basic (or overbased) form. Overbasing provides an alkaline reserve which, when applied in lubricating oil compositions, reacts with and neutralizes acidic compounds formed during the operation of the engine in which the composition is applied. Thus, sludge which may arise is maintained in dispersion while acids which would enhance sludge formation are neutralized.

EP-A-248 465 and -267 658 describe such overbased materials and processes for making them comprising the neutralization of an organic carboxylic acid with alkaline earth metal hydroxides or oxides in the presence of a hydrocarbon solvent and an alcohol promoter and water to provide such overbased lubricating oil detergent additives, including the neutralization of alkyl salicylic acids to produce overbased calcium salts of such acids.

Such overbased additives are in the form of concentrates comprising colloidal particles of basic material stabilised in a liquid medium (or diluent or base oil) by ions of the acidic material, sometimes referred to as surfactant or soap. Desirable properties of such an additive include a high total base number (TBN), good handleability to enable it to be readily admixed to make a final lubricant, and a high active ingredient content to maximise the efficiency of the additive. Unfortunately, these desirable properties may conflict with one another: a high active ingredient content may generate handleability problems by causing the viscosity to become unacceptably high. EP-A-0 267 658, for example, describes overbased additives, wherein the surfactant is a salicylate, which, although having good basic and handleability properties, have active ingredient contents that do not exceed 60 mass %. Overbased detergents, wherein the surfactant is an organic carboxylate, having a high TBN and a handleable viscosity, that also have a high active matter content, have now surprisingly been provided.

Thus, a first aspect of the present invention is an overbased alkaline earth metal, such as Ca or Mg, detergent lubricant additive comprising, as a surfactant for the additive, a major proportion of an organic substantially aromatic carboxylate, the additive having:
  (a) a TBN of 200 or greater, or 250 or greater, or 300 or greater such as 300 to 500, for example 300 to 400;
  (b) an active ingredient content of 70 mass % or greater, such as up to 95, 90, 85 or 80, mass %, active ingredient being all matter other than base oil;
  (c) a kinematic viscosity at 100° C. of less than 1000, such as from 50 to less than 1000, for example from 100 to 500, $mm^2 s^{-1}$; and
  (d) a basicity index (BI) of less than 13, preferably less than 10, more preferably less than 8.

A second aspect of the invention is a lubricating oil composition comprising an admixture of an oil of lubricating viscosity, in a major amount, and an additive according to the first aspect of the invention, in a minor amount.

A third aspect of the invention is a method of lubricating a marine diesel engine, such as a trunk piston engine, comprising supplying to the engine a lubricating oil composition according to the second aspect of the invention.

A fourth aspect of the invention is a combination comprising:
  (a) mechanical parts to be lubricated of a marine diesel engine, such as a trunk piston engine; and
  (b) a lubricating oil composition according to the second aspect of the invention.

In this specification:
"Major amount" means in excess of 50 mass % of the composition;
"Minor amount" means less than 50 mass % of the composition, both in respect of the stated additive and in respect of the total mass % of all of the additives present in the composition, reckoned as active ingredient of the additive or additives;
"Comprises or comprising" or cognate words are taken to specify the presence of stated features, steps, integers, or components, but does not preclude the presence or addition of one or more other features, steps, integers, components or groups thereof;
"TBN" is Total Base Number as measured by ASTM D2896;
"Oil-soluble" or "oil-dispersible" do not necessarily indicate that the additive(s) are soluble, dissolvable, miscible or capable of being suspended in oil, in all proportions. They do mean, however, that they are, for example, soluble or stably dispersible in oil to an extent sufficient to exert their intended effect in the environment in which the oil is employed. Moreover, the additional incorporation of other additives may also permit incorporation of higher levels of a particular additive, if desired;
"substantially aromatic" means greater than 50% by weight, preferably greater than 70% by weight, more preferably greater than 80% by weight, most preferably greater than 90% by weight, of the carboxylate is aromatic; and
"basicity index (BI)" is defined as the equivalents ratio of the total alkaline earth metal to the total of organic acid.

It should be noted that the lubricating oil compositions of this invention comprise defined individual, i.e. separate, components that may or may not remain the same chemically before and after mixing.

The features of the invention will now be discussed in further detail as follows:

OVERBASED DETERGENT

In the detergents of the first aspect of the invention, suitable organic substantially aromatic carboxylate detergents are those derived from acids containing a benzene or naphthalene ring and an oil-solubilising group or group having a total of at least 8, in particular at least 12, carbon atoms. Preferred are hydrocarbyl-, particularly alkylsalicylic acids having at least 10 carbon atoms in the alkyl group or groups, in particular 12 to 26, such as 14 to 18 carbon atoms. Preferably, there is only one surfactant. Preferably, a salicylate constitutes the sole surfactant for the additive.

"Hydrocarbyl" means a group composed primarily of carbon and hydrogen atoms, connected via a carbon atom, and that may contain other atom(s) provided they do not substantially alter the hydrocarbon nature of the group.

Other suitable acids that may be used include substituted or unsubstituted aliphatic or cycloaliphatic acids. As examples, there may be mentioned naphthenic acids; and aliphatic acids having more than 8 carbon atoms such as stearic, isostearic, palmitic, myristic, oleic and hydroxystearic acids, and tertiary carboxylic acids.

The detergents may be prepared by treating with an overbasing agent, at a temperature of less than 100° C., a mixture of at least one organic substantially aromatic surfactant, at least one basic calcium compound and oil. The detergent is optionally subjected to at least one heat-soaking step. After heat-soaking, the detergent is preferably subjected to second treatment with an overbasing agent at a temperature less than 100° C. The second overbasing step is also preferably followed by a heat-soaking step. The detergent preferably has a TBN of at least 300 mgKOH/g. During heat-soaking, the mixture is maintained, without addition of any further chemical reagents, in a selected temperature range, which is normally equal to or higher than the temperature at which carbonation is effected. Temperatures at which heat-soaking may be carried out are typically in the range of from 15° C. to just below the reflux temperature of the reaction mixture, preferably 25 to 60° C.; the temperature should be such that substantially no materials (for example, solvents) are removed from the system during the heat-soaking step. Heat-soaking may be carried out for any suitable period, advantageously for at least 30 minutes, advantageously for at least 45 minutes, preferably for at least 60 minutes, especially for at least 90 minutes.

Examples of suitable overbasing agents are carbon dioxide, a source of boron, for example boric acid, sulphur dioxide, hydrogen sulphide and ammonia. The most preferred overbasing agent is carbon dioxide and, for convenience, the treatment with overbasing agent will in general be referred to as 'carbonation'.

Basic calcium compounds for use in manufacture of the overbased detergents include calcium oxide, hydroxide, alkoxides, carboxylates and a mixture thereof.

The mixture to be overbased by the overbasing agents should normally contain water, and may also contain one or more solvents, promoters or other substances commonly used in overbasing processes. Preferred solvents are toluene, methanol and a mixture thereof. Preferred promoters are methanol and water.

Carbonation is effected at a temperature of less than 100° C. Preferably, carbonation is effected at a temperature of less than 80° C., more preferably less than 60° C., even more preferably less than 40° C. and most preferably less than 35° C. Carbonation is preferably effected at atmospheric pressure.

The detergents may, for example, be prepared by a batch process comprising the following steps:
  (a) neutralising an organic substantially aromatic acid, such as an oil-soluble alkylsalicylic acid, with excess calcium hydroxide in the presence of an organic diluent oil, a liquid monohydric alcohol and water:
  (b) in a first carbonation step, carbonating the mixture with carbon dioxide;
  (c) raising and then lowering the temperature of the mixture;
  (d) providing more calcium hydroxide and, in a second carbonation step, carbonating the mixture with carbon dioxide;
  (e) raising the temperature of the mixture and providing more diluent oil; and
  (f) removing solvents and water and, optionally filtering.

Alternatively, the detergents may be prepared, in some embodiments, by a process analogous to the above, but involving a single carbonation step.

The overbased detergents are useful as additives for oil-based compositions, for example, lubricants or greases. The amount of overbased detergent to be included in the oil-based composition depends on the type of composition and its proposed application: lubricants for marine applications typically contain 0.5 to 18 mass % of overbased detergent, on an active ingredient basis based on the final lubricant, while automotive crankcase lubricating oils typically contain 0.01 to 6 mass % of overbased detergent, on an active ingredient basis based on the final lubricant.

LUBRICATING OIL COMPOSITIONS

To provide the second aspect of the invention, the overbased detergents may be incorporated into an oil of lubricating viscosity (or base stock) in any convenient way. Thus, they may be added directly to the oil by dispersing or dissolving them in the oil at the desired concentration optimally with the aid of a suitable solvent such as toluene or cyclohexane, and at ambient or elevated temperature.

Because the detergents of the invention possess both high TBN and high active matter content, it is possible to blend lubricating oil compositions that have both relatively high TBN and high organic substantially aromatic carboxylate surfactant concentrations, at lower detergent treat rates than hitherto.

A particular problem associated with marine engine lubrication occurs when the engine is a trunk piston marine diesel engine (ie a medium-speed, four-stroke engine). Their manufacturers commonly design them to use a variety of diesel fuels, ranging from good quality high distillate fuel with low sulfur and low asphaltene content to poorer quality intermediate of heavy fuel such as "Bunker C" or residual fuel oil with generally higher sulfur and asphaltene content. Lubricants used in such engines often become contaminated with asphaltene components from the fuel, leading to cleanliness problems in service, sometimes referred to as "black paint".

The lubricating oil compositions of this invention have been found to be particularly efficacious in mitigating the "black paint" problem.

The base stock for the composition may be synthetic or natural.

Synthetic base stocks include alkyl esters of dicarboxylic acids, polyglycols and alcohols; poly-α-olefins, including polybutenes; alkyl benzenes; organic esters of phosphoric acids; and polysilicone oils.

Natural base stocks include mineral lubricating oils which may vary widely as to their crude source, for example, as to whether they are paraffinic, naphthenic, mixed, or paraffinic-naphthenic, as well as to the method used in their production, for example, their distillation range and whether they are straight run or cracked, hydrofined, or solvent extracted.

Lubricating oil base stocks suitable for use in crankcase lubricants conveniently have a viscosity of 2.5 to 12 $mm^2/s$, at 100° C., although base stocks with other viscosities may be used, for example, bright stock.

Lubricating oil base stocks suitable for use in marine lubricants conveniently have a viscosity of typically 3 to 15 $mm^2/s$, at 100° C., although base stocks with other viscosities may also be used. Thus, for example, bright stocks, which typically have a viscosity of 30 to 35 $mm^2/s$, at 100° C. may be used.

Additional additives may be incorporated in the composition to enable it to meet particular requirements. Examples of additional additives which may be included in lubricating oil compositions containing an overbased detergent in accordance with the invention are viscosity index improvers, corrosion inhibitors, oxidation inhibitors or antioxidants, friction modifiers, dispersants, other detergents, metal rust inhibitors, anti-wear agents, pour point depressants, and anti-foaming agents. Lubricating oils suitable for use in marine engines advantageously include a dispersant and an antiwear agent as additional additives and may also contain other additives, for example, additional antioxidants, antifoaming agents and/or rust inhibitors. Certain of the additional additives specified below are more appropriate for use in lubricants for automobile engines than for use in lubricants for marine engines.

Viscosity index improvers (or viscosity modifiers) impart high and low temperature operability to a lubricating oil and permit it to remain shear stable at elevated temperatures and also exhibit acceptable viscosity or fluidity at low temperatures. Suitable compounds for use as viscosity modifiers are generally high molecular weight hydrocarbon polymers, including polyesters, and viscosity index improver dispersants, which function as dispersants as well as viscosity index improvers. Oil-soluble viscosity modifying polymers generally have weight average molecular weights of from about 10,000 to 1,000,000, preferably 20,000 to 500,000, as determined by gel permeation chromatography or light scattering methods.

Corrosion inhibitors reduce the degradation of metallic parts contacted by the lubricating oil composition. Thiadiazoles, for example those disclosed in U.S. Pat. Nos. 2,719,125, 2,719,126 and 3,087,932, are examples of corrosion inhibitors for lubricating oils.

Oxidation inhibitors, or antioxidants, reduce the tendency of mineral oils to deteriorate in service, evidence of such deterioration being, for example, the production of varnish-like deposits on metal surfaces and of sludge, and viscosity increase. Suitable oxidation inhibitors include sulphurized alkyl phenols and alkali or alkaline earth metal salts thereof; diphenylamines; phenyl-naphthylamines; and phosphosulphurized or sulphurized hydrocarbons.

Other oxidation inhibitors or antioxidants which may be used in lubricating oil compositions comprise oil-soluble copper compounds. The copper may be blended into the oil as any suitable oil-soluble copper compound. By oil-soluble it is meant that the compound is oil-soluble under normal blending conditions in the oil or additive package. The copper may, for example, be in the form of a copper dihydrocarbyl thio- or dithio-phosphate. Alternatively, the copper may be added as the copper salt of a synthetic or natural carboxylic acid, for example, a $C_8$ to $C_{18}$ fatty acid, an unsaturated acid, or a branched carboxylic acid. Also useful are oil-soluble copper dithiocarbamates, sulphonates, phenates, and acetylacetonates. Examples of particularly useful copper compounds are basic, neutral or acidic copper $Cu^I$ and/or $Cu^{II}$ salts derived from alkenyl succinic acids or anhydrides.

Copper antioxidants will generally be employed in an amount of from about 5 to 500 ppm by weight of the copper, in the final lubricating composition.

Friction modifiers and fuel economy agents which are compatible with the other ingredients of the final oil may also be included. Examples of such materials are glyceryl monoesters of higher fatty acids, esters of long chain polycarboxylic acids with diols, oxazoline compounds, and oil-soluble molybdenum compounds.

Dispersants maintain oil-insoluble substances, resulting from oxidation during use, in suspension in the fluid, thus preventing sludge flocculation and precipitation or deposition on metal parts. So-called ashless dispersants are organic materials which form substantially no ash on combustion, in contrast to metal-containing (and thus ash-forming) detergents. Borated metal-free dispersants are also regarded herein as ashless dispersants. Suitable dispersants include, for example, derivatives of long chain hydrocarbon-substituted carboxylic acids in which the hydrocarbon groups contain 50 to 400 carbon atoms, examples of such derivatives being derivatives of high molecular weight hydrocarbyl-substituted succinic acid. Such hydrocarbyl-substituted carboxylic acids may be reacted with, for example, a nitrogen-containing compound, advantageously a polyalkylene polyamine, or with an ester. Particularly preferred dispersants are the reaction products of polyalkylene amines with alkenyl succinic anhydrides.

A viscosity index improver dispersant functions both as a viscosity index improver and as a dispersant. Examples of viscosity index improver dispersants suitable for use in lubricating compositions include reaction products of amines, for example polyamines, with a hydrocarbyl-substituted mono- or dicarboxylic acid in which the hydrocarbyl substituent comprises a chain of sufficient length to impart viscosity index improving properties to the compounds.

Examples of dispersants and viscosity index improver dispersants may be found in EP-A-24146.

Additional detergents and metal rust inhibitors include the metal salts, which may be overbased, of sulphonic acids, alkyl phenols, sulphurized alkyl phenols, alkyl salicylic acids, thiophosphonic acids, naphthenic acids, and other oil-soluble mono- and dicarboxylic acids. Representative examples of detergents/rust inhibitors, and their methods of preparation, are given in EP-A-208 560.

Antiwear agents, as their name implies, reduce wear of metal parts. Zinc dihydrocarbyl dithiophosphates (ZDDPs) are very widely used as antiwear agents. Especially preferred ZDDPs for use in oil-based compositions are those of the formula $Zn[SP(S)(OR^1)(OR^2)]_2$ wherein $R^1$ and $R^2$ contain from 1 to 18, and preferably 2 to 12, carbon atoms.

Pour point depressants, otherwise known as lube oil flow improvers, lower the minimum temperature at which the fluid will flow or can be poured. Such additives are well known. Foam control may be provided by an antifoamant of the polysiloxane type, for example, silicone oil or polydimethyl siloxane.

Some of the above-mentioned additives may provide a multiplicity of effects; thus for example, a single additive may act as a dispersant-oxidation inhibitor. This approach is well known and need not be further elaborated herein.

When lubricating compositions contain one or more of the above-mentioned additives, each additive is typically blended into the base oil in an amount which enables the additive to provide its desired function. Representative effective amounts of such additives, when used in crankcase lubricants, are as follows:

| Additive | Mass % a.i.* (Broad) | Mass % a.i.* (Preferred) |
| --- | --- | --- |
| Viscosity Modifier | 0.01–6 | 0.01–4 |
| Corrosion Inhibitor | 0.01–5 | 0.01–1.5 |
| Oxidation Inhibitor | 0.01–5 | 0.01–1.5 |
| Friction Modifier | 0.01–5 | 0.01–1.5 |
| Dispersant | 0.1–20 | 0.1–8 |

-continued

| Additive | Mass % a.i.* (Broad) | Mass % a.i.* (Preferred) |
|---|---|---|
| Detergents/rust inhibitors | 0.01–6 | 0.01–3 |
| Anti-wear Agent | 0.01–6 | 0.01–4 |
| Pour Point Depressant | 0.01–5 | 0.01–1.5 |
| Anti-Foaming Agent | 0.001–3 | 0.001–0.15 |
| Mineral or Synthetic Base Oil | Balance | Balance |

*Mass % active ingredient based on the final oil.

Typical proportions for additives for a TPEO (a trunk piston engine oil) are as follows:

| Additive | Mass % a.i.* (Broad) | Mass % a.i.* (Preferred) |
|---|---|---|
| Detergent(s) | 0.5–15 | 2–12 |
| Dispersant(s) | 0.5–5 | 1–3 |
| Anti-wear agent(s) | 0.1–1.5 | 0.5–1.3 |
| Oxidation inhibitor | 0.2–2 | 0.5–1.5 |
| Rust inhibitor | 0.03–0.15 | 0.05–0.1 |
| Pour point depressant | 0.03–0.15 | 0.05–0.1 |
| Mineral or synthetic base oil | Balance | Balance |

*Mass % active ingredient based on the final oil.

Typical proportions for additives for a MDCL (a marine diesel cylinder lubricant) are as follows:

| Additive | Mass % a.i.* (Broad) | Mass % a.i.* (Preferred) |
|---|---|---|
| Detergent(s) | 1–18 | 3–15 |
| Dispersant(s) | 0.5–5 | 1–3 |
| Anti-wear agent(s) | 0.1–1.5 | 0.5–1.3 |
| Pour point depressant | 0.03–0.15 | 0.05–0.1 |
| Mineral or synthetic base oil | Balance | Balance |

*Mass % active ingredient based on the final oil.

When a plurality of additives are employed it may be desirable, although not essential, to prepare one or more additive packages comprising the additives, whereby several additives can be added simultaneously to the base oil to form the lubricating oil composition. Dissolution of the additive package(s) into the lubricating oil may be facilitated by solvents and by mixing accompanied with mild heating, but this is not essential. The additive package(s) will typically be formulated to contain the additive(s) in proper amounts to provide the desired concentration in the final formulation when the additive package(s) is/are combined with a predetermined amount of base lubricant. Thus, one or more overbased detergents in accordance with the present invention may be added to small amounts of base oil or other compatible solvents together with other desirable additives to form additive packages containing active ingredients in an amount, based on the additive package, of, for example, from about 2.5 to about 90 mass %, and preferably from about 5 to about 75 mass %, and most preferably from about 8 to about 60 mass % by weight, additives in the appropriate proportions with the remainder being base oil.

The final formulations may typically contain about 5 to 40 mass % of the additive package(s) with the remainder being base oil.

EXAMPLES

The following Examples illustrate, but in no way limit, the invention.

Example 1

Preparation of Overbased Calcium Salicylate Detergent Additive

Toluene (453 g), methanol (296 g), water (27 g), and diluent oil (19 g; SN150) were introduced into a reactor and mixed while maintaining the temperature at approximately 20° C. Calcium hydroxide ($Ca(OH)_2$) (142 g) was added, and the mixture was heated to 40° C., with stirring. To the slurry obtained in this way was added alkylsalicylic acid (495 g) and toluene (100 g) followed by a further quantity (20 g) of toluene.

After neutralization of the alkylsalicylic acid by the calcium hydroxide, the temperature of the mixture was reduced to approximately 28° C., and was maintained at approximately 28° C. while carbon dioxide (50 g) was injected into the mixture over a period of 90 to 120 minutes. The temperature was then raised to 60° C. over 60 minutes, following which the mixture was cooled to a temperature of approximately 28° C. over 30 minutes. At 28° C., a further quantity of calcium hydroxide (98 g) was added and then the temperature was maintained at approximately 28° C. while carbon dioxide (50 g) was again injected into the mixture over a period of 90 to 120 minutes. After this second carbonation step, the temperature was raised to 60° C. over 90 minutes. During this heat treatment period, when the temperature reached 45° C., a further charge of diluent oil (167 g) was added.

To complete the synthesis, the produce was heated from 60 to 160° C. in about six hours to remove the solvents and water. This solvent stripping process was performed in three stages:

1. under atmospheric pressure to 114° C., at which point a final charge of diluent oil (50 g) was added.
2. under a pressure of 500 mbar between 114° C. and 125° C.
3. under a pressure of 250 mbar between 125° C. and 160° C.

Finally, the product was filtered to remove sediment.

Characteristics of the overbased calcium salicylate detergent additive made by this process were as follows:

TBN=364 mgKOH/g (measured by ASTM D2896)

Kv100=217 $mm^2s^{-1}$ (measured by ASTM D445)

Active ingredient content=76 mass % (calculated as, [mass of final product—mass of base oil]/[mass of final product])

Basicity Index (BI)=6.0

Example 2

Single Carbonation 453 g toluene, 296 g methanol, 27 g water, and 19 g of diluent oil (SN150) were introduced into a reactor and mixed while maintaining the temperature at approximately 20° C. Calcium hydroxide ($Ca(OH)_2$) (206 g) was added, and the mixture was heated to 40° C., with stirring. To the slurry obtained in this way was added 588 g of alkylsalicylic acid and 100 g of toluene followed by a further quantity (20 g) of toluene.

After neutralization of the alkylsalicylic acid by the calcium hydroxide, the temperature of the mixture was reduced to approximately 28° C., and was maintained at approximately 28° C. while carbon dioxide (81 g) was injected into the mixture over a period of 210 minutes. The temperature was then raised to 60° C. over 90 minutes. During this heat treatment period, when the temperature reached 45° C., a further charge of diluent oil (84 g) was added.

To complete the synthesis, the product was heated from 60 to 160° C. in about six hours to remove the solvents and water. This solvent stripping process was performed in three stages:

1. under atmospheric pressure to 114° C., at which point a final charge of diluent oil (84 g) was added
2. under a pressure of 500 mbar between 114° C. and 125° C.
3. under a pressure of 250 mbar between 125° C. and 160° C.

Finally, the product was filtered to remove sediment. Characteristics of the overbased detergent made by this process are as follows:

TBN=309 mgKOH/g (measured by ASTM D2896)
Kv100=299cSt (measured by ASTM D445)
Active ingredient content=81% (calculated as, [mass of final product—mass of base oil]/[mass of final product])
Basicity Index (BI)=4.3

Example 3

Preparation of Lubricating Oil Composition

An overbased calcium salicylate detergent such as prepared in Example 1 was blended with an oil of lubricating viscosity at a treat rate of only 8.3% to give a composition of 30 TBN and a salicylate (surfactant) content of 43 mmol/kg.

What is claimed is:

1. An overbased alkaline earth metal detergent lubricant additive consisting essentially of, as a surfactant for the additive, alkyl salicylate, the additive having
   (a) a TBN of 200 or greater;
   (b) an active ingredient content of 70 mass or greater, active ingredient being all matter other than base oil;
   (c) a kinematic viscosity at 100° C. of less than 1000 $mm^{2s-1}$;and
   (d) a basicity index (BI) of less than 13.
2. An additive as claimed in claim 1, wherein the alkyl salicylate is alkyl salicylate in which the alkyl group has at least 10 carbon atoms.
3. A lubricating oil composition comprising an admixture of an oil of lubricating viscosity, in a major amount, and an additive as claimed in claim 1, in a minor amount.
4. A composition as claimed in claim 3 in the form of a marine lubricant.
5. A method of lubricating a marine diesel engine comprising supplying to the engine a lubricating oil composition as claimed in claim 4.
6. A combination comprising:
   (a) mechanical parts to be lubricated of a marine diesel engine; and
   (b) a lubricating oil composition as claimed in claim 4.
7. The additive as claimed in claim 1, wherein saidalkaline earth metal is Ca or Mg.
8. The additive as claimed in claim 1, wherein said TBN is 250 or greater.
9. The additive as claimed in claim 8, wherein said TBN is 300 or greater.
10. The additive as claimed in claim 1, wherein said active ingredient content is 85 mass % or greater.
11. The additive as claimed in claim 1, wherein said kinematic viscosity at 100° C. is from 100 to 500 $mm^2s^{-1}$.
12. The additive as claimed in claim 1, wherein said basicity index is less than 10.
13. The additive as claimed in claim 12, wherein said basicity index is less than 8.
14. The composition as claimed in claim 4, in the form of a trunk piston marine engine oil or a marine cylinder oil.

* * * * *